United States Patent [19]

Gebhard et al.

[11] 4,393,718
[45] Jul. 19, 1983

[54] ASSEMBLY FOR STRESS TESTING MATERIAL UNDER HIGH TEMPERATURES

[75] Inventors: Werner Gebhard, Forsbach; Claus Kroder, Cologne, both of Fed. Rep. of Germany

[73] Assignee: Deutsche Forschungs-und Versuchsanstalt für Luft-und Raumfahrt e.V., Fed. Rep. of Germany

[21] Appl. No.: 274,573

[22] Filed: Jun. 17, 1981

[30] Foreign Application Priority Data

Jun. 20, 1980 [DE] Fed. Rep. of Germany ....... 3023063

[51] Int. Cl.³ .............................................. G01N 3/04
[52] U.S. Cl. ......................................... 73/859; 374/49
[58] Field of Search ................. 73/859, 860, 826, 831, 73/833, 834; 374/49

[56] References Cited

U.S. PATENT DOCUMENTS 1,122,289 12/1914 Loveland ............................... 73/859
3,107,522 10/1963 Bonewits ............................... 73/859
4,080,824 3/1978 Starks ..................................... 73/859

Primary Examiner—Jerry W. Myracle
Attorney, Agent, or Firm—Neil F. Markva

[57] ABSTRACT

An assembly as used to test material in a specimen within a high temperature range. The specimen or workpiece is clamped into a clamping mechanism having two clamping heads that are movably disposed with respect to each other. A divided workpiece end holder is disposed within an inwardly enlarged opening form on the facing front walls of each clamping head. A measuring apparatus including two elongation measurement holders are disposed at two laterally displaced locations along the length of the workpiece or specimen. A shoulder configuration is located at the laterally displaced locations on the workpiece. As the specimen is pulled apart by the clamping mechanisms located at each end thereof, the material between the shoulders is elongated. A particular rod and tube arrangement is used to measure the relative movement occurring between the elongation measurement holders disposed at the shoulder locations on the workpiece.

5 Claims, 4 Drawing Figures

ASSEMBLY FOR STRESS TESTING MATERIAL UNDER HIGH TEMPERATURES

FIELD OF THE INVENTION

The invention relates to a tensile stress testing assembly for testing material under high temperatures. More particularly, the assembly comprises two clamping heads secured to a respective shaft so that the heads move apart while gripping the ends of the workpiece.

BACKGROUND OF THE INVENTION

The increasing demand of materials being used under high temperature conditions such as in gas turbine construction requires the materials to be tested very carefully at high temperatures or under similar high temperature conditions. Presently, maximum temperatures of 950° C. are usable with clamping units composed of metal and being used in an oxidizing atmosphere. The dimensional stability and resistance of the clamping mechanism cannot be ensured when metal is being used because the metal is no longer resistant to oxidation at temperatures higher than 950° C. Consequently, deformations may occur as noted and furthermore the specimen or workpiece may not be easily removed from the clamping mechanism after the assembly has been exposed to the higher temperatures.

SUMMARY OF THE INVENTION

The assembly for tensile stress testing material under high temperature conditions includes clamping heads composed of a non-metallic, high temperature resistant material such as a ceramic material. The structural configuration of the clamping mechanism includes clamping heads having an inwardly enlarged opening located at the front walls which face each other. A divided or bipartite workpiece end holder is mounted within the enlarged opening and includes a longitudinal aperture for the passage of the specimen or workpiece. The rear side of the workpiece end holder has a support surface for supporting or abutting a thicker head portion located at each end of the workpiece or specimen.

The high temperature resistant ceramic materials may be used for temperatures up to about 1600° C. Thus, such materials are far superior to the metallic materials now used to form the known tensile stress testing devices. However, the constructional features characteristic of a metallic clamping mechanism cannot be transferred to a ceramic material construction. That is, specific constructional features are necessarily associated with the use of ceramic materials. For example, ceramic materials cannot be machined to remove it from the specimens. Furthermore, specific constructional features are required because of the brittle nature of the ceramic material.

The divided workpiece end holder is placed around the ends of a shaft-shaped workpiece and then mounted from the inside into the opening of a clamping head. Under tensile stress, the clamping head disposed around the end of the workpiece presses against a support surface at the rear end of the workpiece end holder thereby pressing the holder into the opening toward the front face of the clamping head. The inner opening of the clamping head is conically shaped and the two halves of the workpiece end holder have a correspondingly shaped outer surface. Therefore, as the clamping head pulls away from the center of the workpiece, the end of the workpiece forces the outer conically shaped surface of the holder toward the front face of the clamping head and thereby firmly presses the inside of the holder against the shaft-shaped workpiece thus distributing the clamping force in the longitudinal direction of the workpiece.

The clamping head is a substantially cylindrical, hollow element and contains the conical opening at its front side for mounting the workpiece end holder and for the passage of the end of the shaft-shaped workpiece. Thus, the clamping mechanism consists of only a few elements of a simply design which correspond to the constructional requirements of the parts being made of a ceramic material. A ceramic material which has proved to be particularly suitable is silicon nitride.

Another feature of the invention is the use of a particular configuration to fix the clamping heads onto the shafts which transmit the tension onto the workpiece. Each shaft projects into a longitudinal central opening or bore of the hollow, appertaining clamping head. The shaft and corresponding clamping head have aligned channels or bores which are transverse to the longitudinal axis of the shaft. A pin projects through the aligned transverse channels or openings in the clamping head and the shaft thereby fixing the parts with respect to each other. The transverse channels or bores may be easily produced during the manufacture of the individual workpieces and no after-treatment such as drilling is necessary. The shafts may be composed of ceramic tubes. Because of the tubular construction of the shafts, tensions within the ceramic material are significantly reduced.

Another feature of the invention is directed to a mechanism for effecting strain measurements under high temperatures. Such measurements are often subjected to great difficulty under high temperature conditions. This feature provides particularly constructed elongation measurement holding means for holding the workpiece at laterally displaced locations on the longitudinal axis of the workpiece. The holding means includes a bipartite inner ring fitted into the central opening of an annular jacket ring. The inner ring includes an annular groove which engages a shoulder configuration at each of the laterally displaced locations on the workpiece or specimen. Each holder moves with the respective portions of the workpiece or specimen being pulled apart under high temperature conditions during the stress or creep testing. Measurement of the relative movement taking place between the two holding devices will determine the amount of material elongation of the specimen or workpiece.

The measurement apparatus of this invention provides a particular manner of securing the inner ring to the annular jacket ring. A pair of parallel semi-channels are formed on the facing surfaces of the inner ring and jacket ring to form a bore or open channel therein. Pins are inserted into that open channel which extends in a common plane of both rings. Thus, the rings are locked in a position with respect to each other by the inserted pins so that they are retained against one another and at a respective shoulder structure on the workpiece or specimen.

Another feature of the invention is directed to the use of at least one rod movably mounted within a tube for measuring the amount of displacement between the two elongation measurement holders disposed at the shoulder locations on the workpiece. The outer ends of the rod and tube are disposed at a measuring unit. The rod extends through an opening of one of the holders and is supported at the other holder. The end of the tube is supported on the holder through which the rod extends. As the holders move in a manner corresponding to the elongation of the workpiece, the rod is displaced a corresponding distance within the tube. The measuring unit located at the outer or other ends of the rod and tube measures the relative movements between the two and thereby measures the relative movement between the holders to which the rod and tube are attached. The measuring units can therefore be disposed outside of the immediate high temperature condition zone within which the workpiece is disposed or tested.

BRIEF DESCRIPTION OF DRAWINGS

Other objects of this invention will appear in the following description and appended claims, reference being made to the accompanying drawings forming a part of the specification wherein like reference characters designate corresponding parts in the several views.

DETAILED DESCRIPTION

Figure 1:
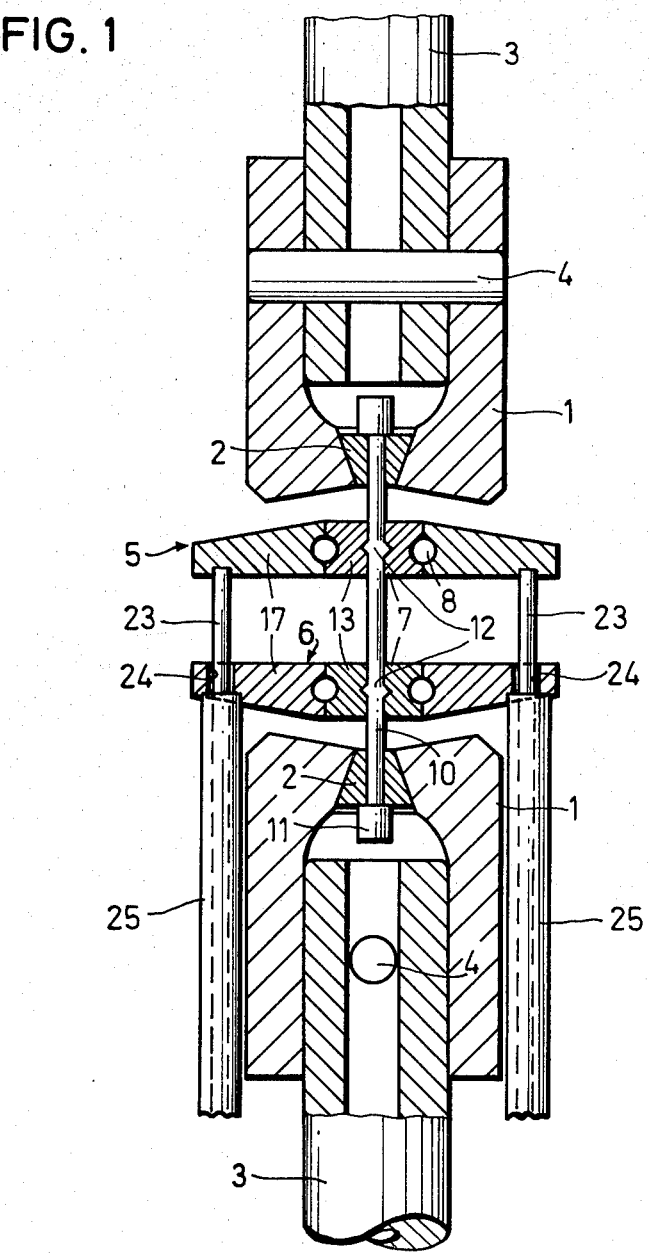
FIG. 1 is a longitudinal sectional view of a tensile stress testing device made in accordance with this invention.
Figure 2:
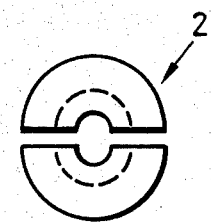
FIG. 2 is a plan view of a bipartite holder used with the testing device of this invention.
Figure 3:
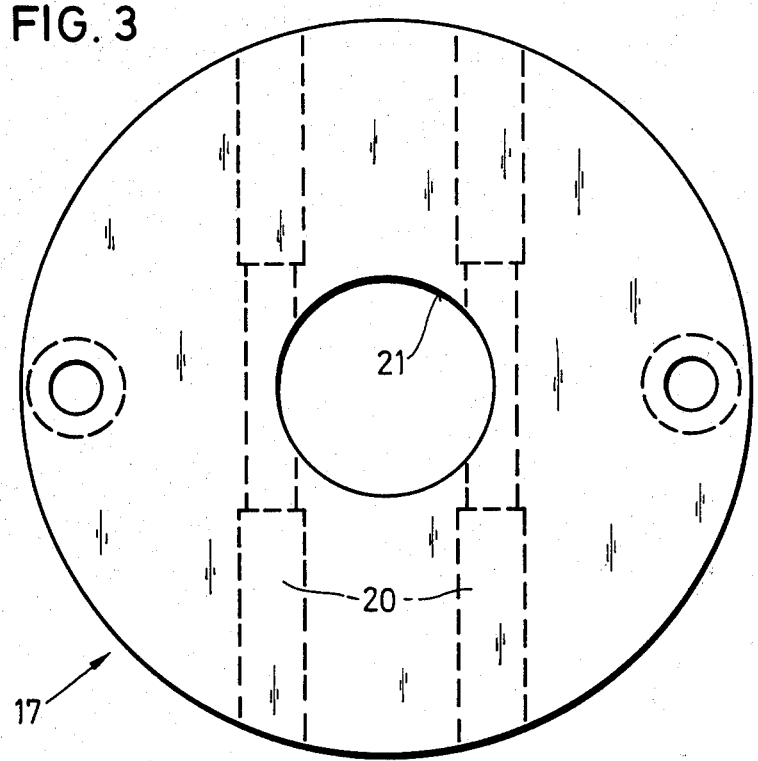
FIG. 3 is a plan view of the jacket ring of an elongation measurement holder made in accordance with this invention.

Referring to FIG. 1, one clamping head 1 is mounted on each of the tubular shafts 3. The strain required for performing tensile stress or tension creep tests is transmitted by a non-illustrated driving unit acting on the tubular shafts 3.

Each clamping head 1 is substantially cylindrical and has an opening located at its front face. Each opening is conically tapered to the front side of each head 1 in which a frusto-conical bipartite holder 2 is mounted. Holders 2 have an elongated hole for the passage of a shaft-shaped specimen or workpiece 10. The thicker head sections 11 located at each end of the workpiece 10 are supported at the rear face of each of the holders 2.

Each clamping head 1 has an axial central opening into which the end of the appertaining shaft 3 projects. A pin 4 extends through aligned transverse channels which are formed in the clamping head 1 and shaft 3. Thus pin 4 locks the clamping head 1 and the shaft 3 together.

Figure 4:
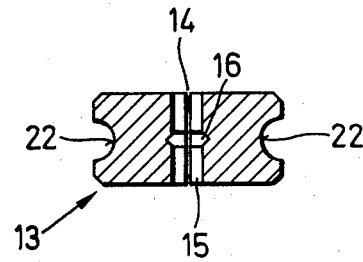
FIG. 4 is a longitudinal sectional view of a internal ring of an elongation measurement holder as shown in FIG. 3.

As shown, as the shafts 3 move apart along the longitudinal axis thereof, the two end heads 11 of specimen 10 are clamped as described thus causing specimen or workpiece 10 to be elongated. Elongation measurement holders 5 and 6 are secured to workpiece 10 and are used to determine the amount of elongation. The workpiece 10 includes annular shoulders 12 on both sides of its axial central area. Each of the measurement holders 5 and 6 includes a divided inner ring 13 surrounded by a jacket ring 17. As shown in FIG. 4, each inner ring 13 is divided along a separating line 14 and has a shaped groove to fit around the shoulders 12 of workpiece 10. Thus, each of the annular halves which forms the closed inner ring 13 includes a longitudinal channel for groove 15 with an annular groove 16 shaped to receive the annular shoulder 12. The particular manner of placement of the inner ring about shoulder 12 is clearly shown in FIG. 1.

Each inner ring 13 fits into the central opening 21 of the respective jacket ring 17. Two channels or bores 20 extend through jacket ring 17 and are parallel to the front annular faces or sides of ring 17 and with respect to each other. Bores 20 partially intersect central opening 21 and thereby form semi-channels or grooves in the area of central opening 21. Further semi-channels or grooves 22 are formed in the cylindrical peripheral area of inner ring 13. Pins 8 inserted into channels 20 lock inner ring 13 rigidly and securely inside jacket ring 17.

A measuring assembly made in accordance with this invention includes a pair of rods 23 movably mounted within a pair of tubes 25 as shown in FIG. 1. The lower ends of rods 23 and tubes 25 extend to a measuring unit (not shown). The two rods 23 are parallel with respect to each other and the longitudinal axis of the specimen 10. The upper ends of rods 23 extend through openings 24 located in the lower measurement holder 6 and abut the lower side of the upper measurement holder 5 as shown. The upper ends or tubes 25 abut the lower side of the lower measurement holder 6.

When the strain is placed on the tubular shaft 3 the specimen 10 begins to stretch along its longitudinal axis. This causes the distance between the shoulders 12 to become elongated and the holders 5 and 6 move outwardly with respect to each other. As the distance between the measurement holders 5 and 6 is widened, the amount of movement must be measured to determine the amount of stress or creep of the material used to make the specimen 10. As the holders 5 and 6 move outwardly, the rods 23 move within the tubes 25. The measuring unit located at the lower ends of the rods 23 and tubes 25 measures the change in the distance between the two annular shoulders 12 of specimen 10 as the measurement holders 5 and 6 move away from each other during the testing of the material in workpiece 10.

Since the material of workpiece 10 is being tested under high temperatures, the clamping heads 1, holders 2, elongation measurement holders 5 and 6, shafts 3 and pins 4 and 8 are made of high temperature resistant materials. In once specific embodiment, clamping heads 1 are composed of ceramic material and shafts 3 are ceramic tubes.

While the assembly for tensile stress testing material under high temperatures has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. An assembly for tensile stress testing material under high temperatures, said assembly comprising:
    (a) two clamping means mounted to move longitudinally with respect to each other and having a structural configuration to hold a workpiece at two laterally displaced locations thereon,
    (b) each clamping means includes a clamping head and a divided workpiece end holder disposed within the clamping head,
    (c) the clamping heads each have a front wall facing each other and an inwardly enlarged opening at their facing front walls, (d) each divided workpiece end holder is mounted in said enlarged opening and contains a longitudinal opening for the passage of the end of the workpiece, (e) the rear side of each workpiece end holder having a support face effective to support a thicker head located at the end of the workpiece, and (f) a measuring apparatus including two laterally displaced elongation measurement holders for engaging the workpiece at two laterally displaced locations thereon which locations are inwardly spaced from the ends of the workpiece, (g) said measurement holders include an annular jacket ring having a central opening and a bipartite inner annular ring mounted within said central opening, (h) each of the sections of said bipartite inner ring having an annular groove facing inwardly with respect to the specimen and having a structural configuration to engage a shoulder formed at each of the two laterally spaced locations on the workpiece.

2. An assembly for tensile stress testing material under high temperatures, said assembly comprising:

(a) two clamping means mounted to move longitudinally with respect to each other and having a structural configuration to hold a workpiece at two laterally displaced locations thereon, (b) each clamping means includes a clamping head and a divided workpiece end holder disposed within the clamping head, (c) the clamping heads each have a front wall facing each other and an inwardly enlarged opening at their facing front walls, (d) each divided workpiece end holder is mounted in said enlarged opening and contains a longitudinal opening for the passage of the end of the workpiece, (e) the rear side of each workpiece end holder having a support face effective to support a thicker head located at the end of the workpiece, and (f) a measuring apparatus including a pair of elongation measurement holder means each having an annular jacket ring and a bipartite inner ring disposed within said jacket ring, (g) each jacket ring including a pair of bores that are parallel with respect to each other and extend through the annular jacket ring and intersects the central opening therein to form open channels along the inside surface of the central opening, (h) each of the sections of the bipartite inner ring have channels disposed on the outside circumferential surface to face the channel sections formed on the inner surface of the central opening of the jacket ring thereby defining a holding bore, and (i) a pair of pins extend through the bores in the inner ring and the location where the inner ring intersects the bore section extending along the central opening of the annular jacket.

3. An assembly for tensile stress testing material under high temperatures, said assembly comprising:

(a) two clamping means mounted to move longitudinally with respect to each other and having a structural configuration to hold a workpiece at two laterally displaced locations thereon, (b) each clamping means includes a clamping head and a divided workpiece end holder disposed within the clamping head, (c) the clamping heads each have a front wall facing each other and an inwardly enlarged opening at their facing front walls, (d) each divided workpiece end holder is mounted in said enlarged opening and contains a longitudinal opening for the passage of the end of the workpiece, (e) the rear side of each workpiece end holder having a support face effective to support a thicker head located at the end of the workpiece, and (f) a measuring apparatus including a pair of elongation measurement holding members laterally displaced with respect to each other and having a structural configuration to engage a workpiece at two laterally displaced locations thereon, and (g) a measuring means, (h) said measuring apparatus including at least one rod movably mounted in a tube wherein the outer ends thereof are connectable to the measuring means, (i) the inner end of the tube is supported on a first one of the measurement holders and the rod extends through said first measurement holder and abuts the second measurement holder, (j) said inner ends of the rod and tube being rigidly secured to the respective measurement holder to move along with the measurement holders as the holders move with respect to each other during tensile testing of the material in the test workpiece whereby the measurement of the relative movement between the rod and tube will result in the corresponding movement between the two elongation measurement holders.

4. An assembly as defined in any one of the claims 1, 2 or 3 wherein each clamping head has a longitudinal central opening and the end of a movably disposed shaft extends into each of the longitudinal central openings of the appertaining clamping head, each clamping head and the end of each shaft disposed therein include aligned bores extending transversely to the longitudinal axis of said shaft and clamping head, a pin projects through said aligned transverse bores to secure the clamping head to the end of said shaft.

5. An assembly as defined in claim 4 wherein each of the shafts are ceramic tubes and each of the clamping heads are composed of a ceramic material.

* * * * *